(12) United States Patent
Lafontaine

(10) Patent No.: US 7,101,368 B2
(45) Date of Patent: *Sep. 5, 2006

(54) CRYO BALLOON FOR ATRIAL ABLATION

(75) Inventor: Daniel M. Lafontaine, Plymouth, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 63 days.

This patent is subject to a terminal disclaimer.

(21) Appl. No.: 10/694,532

(22) Filed: Oct. 27, 2003

(65) Prior Publication Data

US 2004/0143249 A1 Jul. 22, 2004

Related U.S. Application Data

(63) Continuation of application No. 09/849,892, filed on May 4, 2001, now Pat. No. 6,666,858.

(60) Provisional application No. 60/283,301, filed on Apr. 12, 2001.

(51) Int. Cl.
*A61B 18/18* (2006.01)
*A61M 37/00* (2006.01)

(52) U.S. Cl. ..................... 606/21; 604/95.04

(58) Field of Classification Search ............ 606/20–26; 604/95.04
See application file for complete search history.

(56) References Cited

U.S. PATENT DOCUMENTS

| 3,125,096 A | 3/1964 | Antiles et al. |
| 3,712,306 A | 1/1973 | Bryne |
| 4,278,090 A | 7/1981 | van Gerven |
| 4,280,499 A | 7/1981 | Sguazzi |
| 4,784,133 A | 11/1988 | Mackin |
| 4,860,744 A | 8/1989 | Johnson et al. |
| 5,019,042 A | 5/1991 | Sahota |
| 5,078,713 A | 1/1992 | Varney |
| 5,108,390 A | 4/1992 | Potocky et al. |
| 5,139,496 A | 8/1992 | Hed |
| 5,147,355 A | 9/1992 | Friedman et al. |
| 5,190,540 A | 3/1993 | Lee |
| 5,281,215 A * | 1/1994 | Milder ................ 606/20 |
| 5,334,181 A | 8/1994 | Rubinsky et al. |
| 5,334,193 A | 8/1994 | Nardella |
| 5,335,669 A | 8/1994 | Tihon et al. |
| 5,342,301 A | 8/1994 | Saab |
| 5,417,689 A | 5/1995 | Fine |
| 5,423,807 A | 6/1995 | Milder |

(Continued)

FOREIGN PATENT DOCUMENTS

GB 1019028 2/1996

(Continued)

OTHER PUBLICATIONS

Abstract entitled "Argon Beam Coagulation Compared with Cryoablation of Ventricular Subendocardium," *Annals of Thoracic Surgery*, Jan. 1993, 1 page.

(Continued)

*Primary Examiner*—Michael Peffley
(74) *Attorney, Agent, or Firm*—Fish & Richardson P.C.

(57) ABSTRACT

The present invention pertains generally to the field of cryo balloon therapy and the use of cryo balloon therapy catheters to generate cold-induced lesions. The present invention includes a cryo balloon therapy apparatus, comprising a catheter having a proximal and a distal end, a cooling member disposed at the distal end of the catheter, a pull cord coupled to the cooling member, and a sheath that couples the pull cord and the catheter. A method for causing cold-induced necrosis is also disclosed.

20 Claims, 15 Drawing Sheets

U.S. PATENT DOCUMENTS

| | | | |
|---|---|---|---|
| 5,443,470 A * | 8/1995 | Stern et al. | 607/98 |
| 5,454,807 A | 10/1995 | Lennox et al. | |
| 5,501,681 A | 3/1996 | Neuwirth et al. | |
| 5,520,682 A | 5/1996 | Baust et al. | |
| 5,536,252 A | 7/1996 | Imran et al. | |
| 5,624,392 A | 4/1997 | Saab | |
| 5,800,482 A * | 9/1998 | Pomeranz et al. | 607/101 |
| 5,868,735 A * | 2/1999 | Lafontaine | 606/21 |
| 5,902,299 A | 5/1999 | Jayaraman | |
| 5,921,958 A * | 7/1999 | Ressemann et al. | 604/96.01 |
| 5,921,982 A | 7/1999 | Lesh et al. | |
| 5,957,917 A | 9/1999 | Doiron et al. | |
| 5,968,059 A | 10/1999 | Ellis et al. | |
| 5,971,979 A * | 10/1999 | Joye et al. | 606/21 |
| 5,971,983 A | 10/1999 | Lesh | |
| 5,991,650 A | 11/1999 | Swanson et al. | |
| 6,012,457 A | 1/2000 | Lesh | |
| 6,024,740 A | 2/2000 | Lesh et al. | |
| 6,048,329 A | 4/2000 | Thompson et al. | |
| 6,106,518 A | 8/2000 | Wittenberger et al. | |
| 6,117,101 A | 9/2000 | Diederich et al. | |
| 6,123,718 A * | 9/2000 | Tu et al. | 607/113 |
| 6,164,283 A | 12/2000 | Lesh | |
| 6,179,835 B1 | 1/2001 | Panescu et al. | |
| 6,312,749 B1 | 11/2001 | Annicchiarico | |
| 6,321,749 B1 * | 11/2001 | Toti et al. | 128/207.14 |

FOREIGN PATENT DOCUMENTS

| | | |
|---|---|---|
| GB | 2336782 | 11/1999 |
| GB | 2337000 | 11/2000 |
| WO | 97/12557 | 4/1997 |
| WO | 99/27862 | 6/1999 |
| WO | 00/47118 | 8/2000 |

OTHER PUBLICATIONS

Abstract entitled "Cox Maze Operation Without Cryoablation for the Treatment of Chronic Atrial Fibrillation," *Annals of Thoracic Surgery*, Aug. 1995, 1 page.

Abstract entitled "Histologic Study of Chronic Catheter Cryoablation of Atrioventricular Conduction in Swine," *American Heart Journal*, Jun. 1993, 1 page.

Abstract entitled "Intractable Chest Pain in Cardiomyopathy: Treatment by a Novel Technique of Cardiac . . . ," *British Heart Journal*, Dec. 1993, 1 page.

Abstract entitled "Percutaneous Serial Catheterization in Swine: A Practical Approach," *Journal of Investigative Surgery*, Mar.-Apr. 1995, 1 page.

Article entitled "Prostate Cryosurgery Now Reimbursable in Southern California," *Healthcare Technology Management*, published on date even with or prior to Jan. 12, 1999, 1 page.

Abstract entitled "Renal Cryoablation in a Canine Model", *Urology*, May 1996, 1 page.

Cahan, "Five Years of Cryosurgical Experience: Benign and Malignant Tumors with Hemorragic Condistions," *Cryosurgery*, 388-391, published on date even with or prior to Jan. 12, 1999.

Coger et al., "Preservation Techniques for Biomaterials," *The Biomedical Engineering Handbook*, 8 pages, 1995.

Fuller et al., Clinical Applications of Cryobiology, 4 pages, published on date even with or prior to Jan. 12, 1999.

Hunt et al., "Fractures in Cryopreserved Arteries," *Cryobiology*, 31, 506-515 (1994).

Mazur, "Physical-Chemical Factors Underlying Cell Injury in Cryosurgical Freezing," *Cryosurgery*, 32-51, published on date even with or prior to Jan. 12, 1999.

Morris et al., "Effects of Low Temperatures on Biological Membranes," 2 pages, published on date even with or prior to Jan. 12, 1999.

Nataf et al., "Effect of Cold Anoxia and Cryopreservation on Metabolic and Contractile Functions of Human Mammary Artery," *Cryobiology*, 1995, 32:327-333.

Ross et al., Abstract entitled "Cardiac Rhythm Disturbances Due to Caval Occlusion During Hepatic Cryosurgery," *Cryobiology*, Oct. 1994, 1 page.

Schilling et al., "Nature of the Vehicle for Cryopreservation of Human Peripheral Veins: Preservation of Reactivity to Pharmacological Stimuli," *Cryobiology*, 1995, 32:109-113.

Zacarian, "Cryosurgery of Tumors of the Skin and Oral Cavity," 5 pages, published on date even with or prior to Jan. 12, 1999.

\* cited by examiner

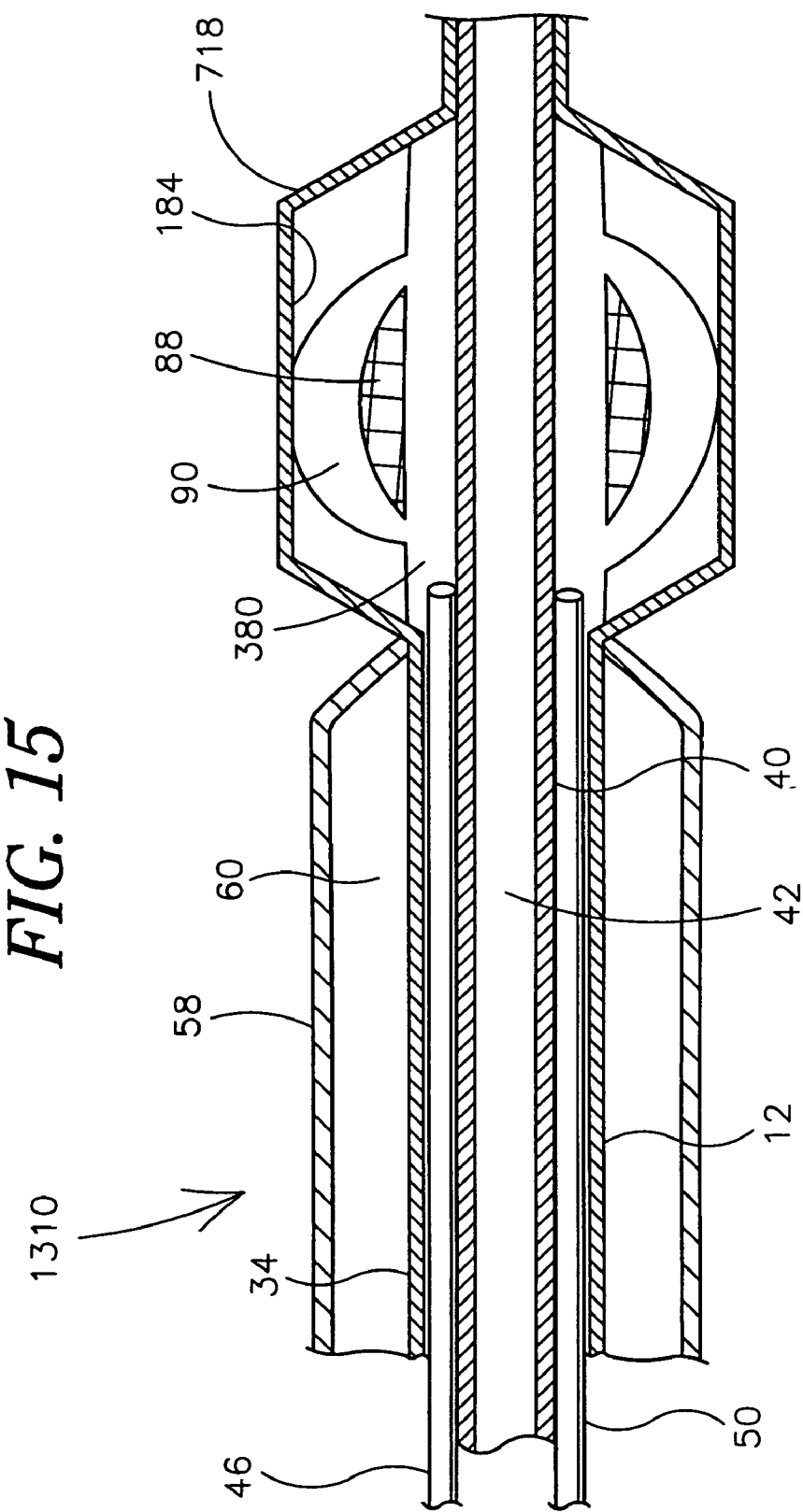

CRYO BALLOON FOR ATRIAL ABLATION

CROSS REFERENCE TO RELATED APPLICATION

This application is a continuation of U.S. patent application Ser. No. 09/849,892, filed May 4, 2001, now issued as U.S. Pat. No. 6,666,858, which claims the benefit of U.S. Provisional Application Ser. No. 60/283,301, filed on Apr. 12, 2001.

FIELD OF THE INVENTION

The present invention pertains generally to the field of cryo balloon therapy. More particularly, the present invention pertains to cryo balloon therapy catheters for use in causing cold-induced necrosis.

BACKGROUND OF THE INVENTION

A number of medical conditions may be treated using ablative techniques or devices. Ablative techniques, generally, result in the killing of abnormal tissue at an area of interest. Killing the abnormal tissue may result in an efficacious treatment for a medical condition. For example, atrial fibrillation may be the result of abnormal electrical activity in the left atrium and the pulmonary vein, and may be treatable by ablation of the abnormal tissue within the left atrium and/or the pulmonary vein.

Atrial fibrillation is a serious medical condition that is the result of abnormal electrical activity within the heart. This abnormal activity may occur at regions of the heart including the sino-atrial (SA) node, the atrioventricular (AV) node, the bundle of His, or within other areas of cardiac tissue. Moreover, atrial fibrillation may be caused by abnormal activity within a isolated focal center within the heart. It is believed that these foci can originate within the pulmonary vein, particularly the superior pulmonary veins.

Minimally invasive techniques have been described that use ablation catheters to target the pulmonary vein with the hope of ablating foci having abnormal electrical activity. The techniques typically are characterized by application of energy to cause lesions within the foci or other areas possessing abnormal electrical activity.

Some ablation devices utilize radio frequency (RF) energy for ablation, including the device disclosed in U.S. Pat. No. 6,024,740 to Lesh et al. The RF energy devices may be used to ablate an area of interest with heat. The use of RF energy for ablation may, however, lead to untoward healing responses such as collagen build up at the area of interest after treatment. Moreover, RF ablation of within an atrium may decrease atrial output. A need, therefore, exists for ablative devices and methods that include improved healing responses.

An alternative treatment strategy has been developed that uses cooling energy for ablation. This method, termed cryoplasty or cryo balloon therapy, may be used to cool the lesion to freeze a portion of the affected area. For example, cryo balloon therapy may be used to freeze a lesion within a blood vessel that might otherwise lead to restenosis or recoil.

In addition to its potential utility in preventing and slowing restenosis and addressing recoil, cryo balloon therapy may be used for ablation techniques. For example, cryo balloon therapy may be efficacious in varicose vein treatment of incompetent valves, valvular disease, mitral valve regurgitation therapy, atrial fibrillation, gastric reflux disease, gastro esophageal reflux disease, GURD, esophageal disease, cancer treatment including stomach or uterine cancer, etc.

Uses of cryo balloon therapy include cold-induced killing of cells within the body. When the target area is located within the heart or pulmonary vasculature, it may be important to precisely control the cryo balloon therapy catheter to kill only the desired tissue. Moreover, the irregular shapes of blood vessels and heart chambers may make it difficult to steer a cryo balloon therapy catheter to a precise location. A need, therefore, exists for a cryo balloon therapy catheter with a desirable level of control.

SUMMARY OF THE INVENTION

The present invention comprises a refinement of cryo balloon therapy catheters. More particularly, the present invention comprises a cryo balloon therapy apparatus that may be useful in treating a number of medical conditions where cold-induced necrosis may prove beneficial. For example, the cryo balloon therapy apparatus may be used to treat varicose vein treatment of incompetent valves, valvular disease, mitral valve regurgitation therapy, gastric reflux disease, gastro esophageal reflux disease, GURD, esophageal disease, cancer treatment including stomach or uterine cancer, pulmonary vein ablation, etc.

The cryo balloon therapy apparatus may comprise a catheter having a proximal end, a distal end, and a cooling member disposed at the distal end. A pull cord may be coupled to the cooling member. The cryo balloon therapy apparatus may further comprise a sheath that couples the pull cord to the catheter. The use of the sheath in conjunction with the pull cord may allow the cooling member to be easily manipulated and steered by moving the pull cord.

The cooling member may be comprised of an outer member disposed over an inner member. Coolant may be transferred to the inner member in order to cool the cooling member to a temperature appropriate for causing cold-induced necrosis, which may be appropriate for a particular medical procedure. Preferably, coolant may be sprayed onto the inner member in order to facilitate heat transfer between the cooling member and an area of interest.

The cooling member may further comprise an electrode and an electric lead. Alternatively, the cooling member may further comprise a pad printed conductive electrode having an electrical lead. According to this embodiment, the electrode may be used to determine the electrical activity of tissue at an area of interest.

Multiple alternative embodiments of the cooling member are also disclosed. For example, the cooling member may further comprise a support member that may help to prevent the cooling member from rupturing. The cooling member may include a cryo balloon therapy chamber disposed on the mesh cage, the cryo balloon therapy chamber connected to a coolant source. The cryo balloon therapy chamber may further comprise a cryo balloon therapy ring. In another preferred embodiment, the cooling member may further comprise a heat exchange surface that may be slidable, a slidable and rotatable sprayer, or a cryo balloon therapy assembly.

BRIEF DESCRIPTION OF THE DRAWINGS

FIG. 15 is a plan view of a thirteenth alternate cryo balloon therapy apparatus in accordance with the present invention.

DETAILED DESCRIPTION OF THE PREFERRED EMBODIMENTS

Figure 1:
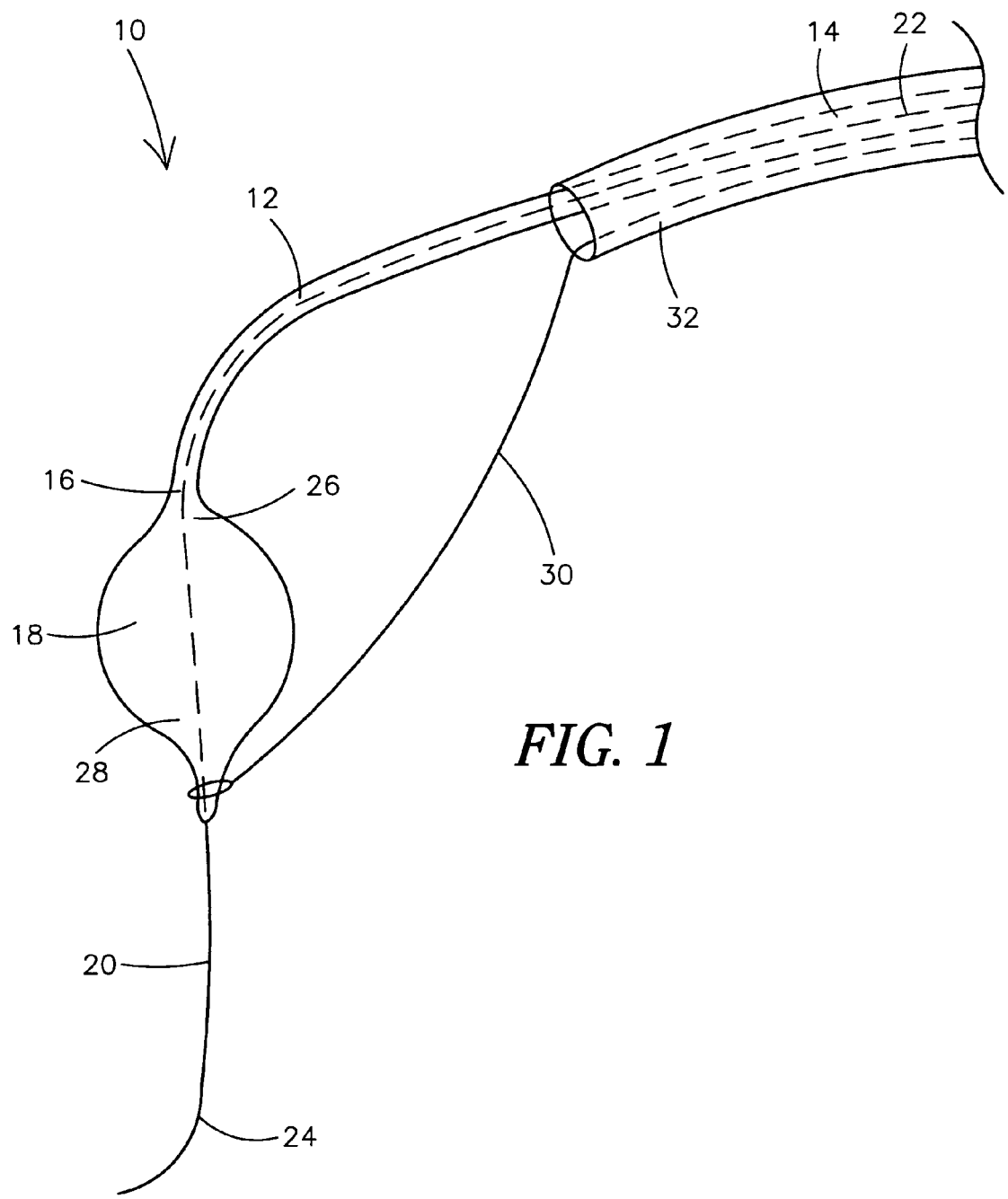
FIG. 1 is a plan view of a cryo balloon therapy apparatus in accordance with the present invention.

The following description should be read with reference to the drawings wherein like reference numerals indicate like elements throughout the several views. The detailed description and drawings represent select embodiments and are not intended to be limiting.

FIG. 1 is a plan view of a cryo balloon therapy apparatus according to a preferred embodiment of the current invention. A cryo balloon therapy apparatus 10 may comprise a catheter 12 having a proximal end 14, a distal end 16, and a cooling member 18 disposed at distal end 16. Preferably, cooling member 18 is a cryo balloon therapy balloon. At least a portion of a guidewire 20 having a proximal end 22 and a distal end 24 may be disposed within catheter 12.

Cooling member 18 may include a proximal end 26 and a distal end 28. A pull cord 30 may be coupled to cooling member 18. For example, pull cord 30 may be disposed at distal end 28 of catheter 12. Multiple embodiments of the current invention include differing pull cords. For example, pull cord 30 may include, but is not limited to, cords, wires, catheters, polymers, tethers, and portions of cryo balloon therapy apparatus 10. For example, pull cord 30 may include catheter 12, guidewire 20, cooling member 18, portions thereof, and combinations thereof.

Cryo balloon therapy apparatus 10 may further comprise a sheath 32. Preferably, sheath 32 couples pull cord 30 to catheter 12. The use of sheath 32 in conjunction with pull cord 30 may allow cryo balloon therapy apparatus 10 to be easily to manipulated and steered. Pull cord 30 can be manipulated through sheath 32 to control the position of cooling member 18. For example, pull cord 30 may be pulled, which may bend catheter 12 slightly into an arc and alter the position of cooling member 18.

Sheath 32 may further comprise a catheter lumen and a pull cord lumen. Preferably, catheter 12 and pull cord 30 pass through the catheter lumen and the pull cord lumen respectively. By including a catheter lumen and a pull cord lumen may improve the ability of a user to manipulate cooling member 18. For example, a catheter lumen and a pull cord lumen may allow catheter 12 and pull cord 30 to become substantially fixed with respect to sheath 32. Therefore, rotation of sheath 32 would accordingly rotate cooling member 18. This may enhance the ability to manipulate and steer cryo balloon therapy apparatus 10.

Figure 2:
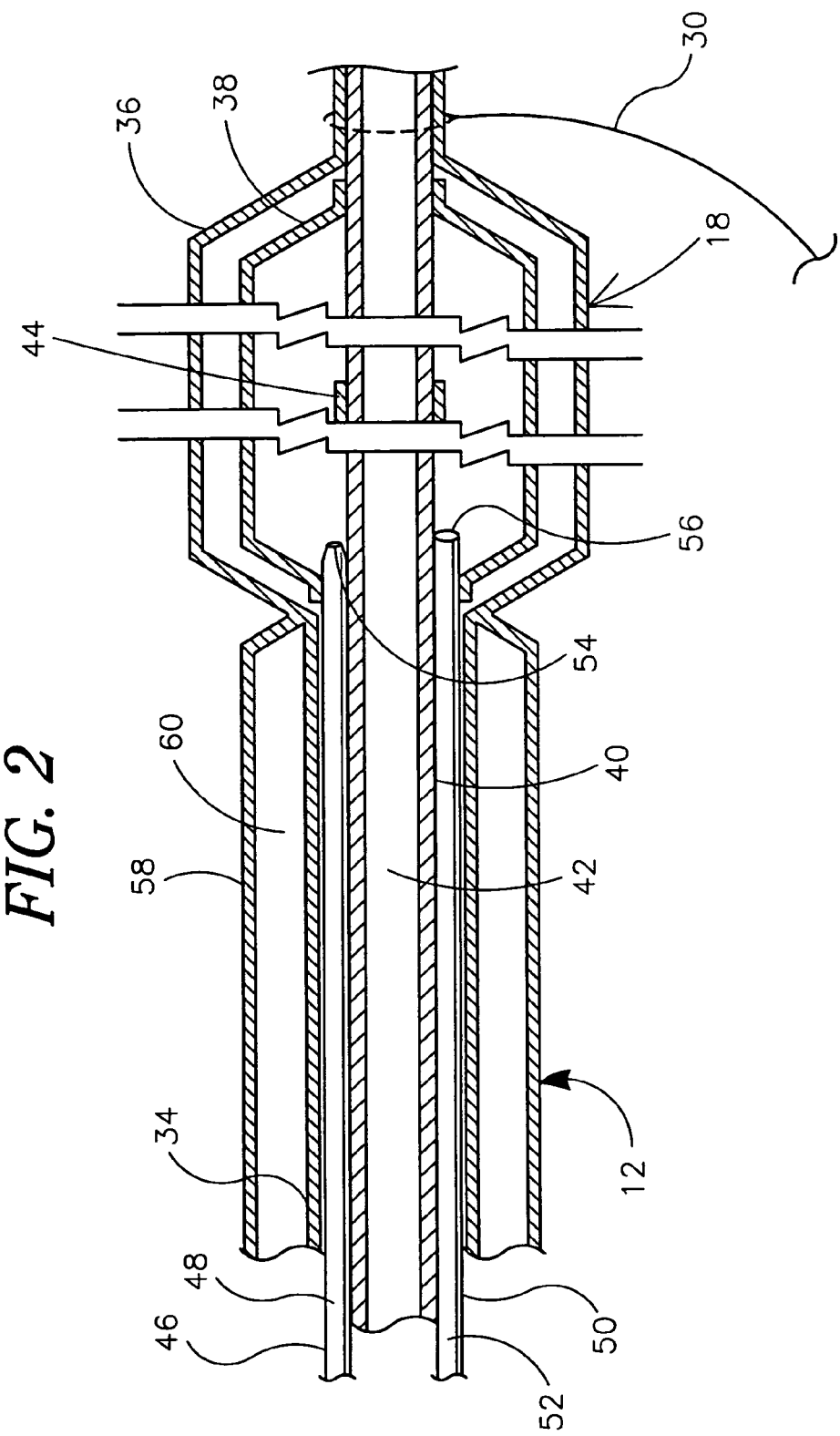
FIG. 2 is a detailed view of a cooling member for use with a cryo balloon therapy apparatus.

FIG. 2 is a preferred embodiment of catheter 12 and cooling member 18. Catheter 12 may include an outer tube 34. Cooling member 18 may comprise an outer member 36 disposed over an inner member 38. Preferably, inner member 38 is a balloon. In an exemplary embodiment, inner member 38 may be a semi-compliant balloon that is about 18 millimeters in diameter. A guidewire tube 40 defining a guidewire lumen 42 can extend through at least a portion of catheter 12. A marker band 44 can be disposed on guidewire tube 40.

Catheter 12 may also include a coolant intake tube 46 defining a coolant lumen 48 in fluid communication within inner member 38. Catheter 12 may also include a drain tube 50 which defines a drain lumen 52 in fluid communication with inner member 38. At the distal end of intake tube 46 is an orifice 54 which preferably has a diameter smaller than that of an orifice 56 at the distal end of drain tube 50. The diameter of orifice 54 could be, for example, about 0.004 inches, or larger or smaller depending upon the diameter of orifice 56.

Those skilled in the art will recognize the various materials and dimensions which can be advantageously used to make the catheter of the present invention. Those elements not found in a conventional angioplasty catheter such as coolant intake tube 46, inner member 38 and drain tube 50 can also be made from materials known to those skilled in the art. For example, intake tube 46 can be a hypotube or polyimide tube having an inside diameter of, for example, between 0.001 to 0.020 inches, but preferably between 0.002 and 0.010 inches. Drain tube 50 can be made from polyimide and have an inside diameter which is preferably greater than the inside diameter of intake tube 46. Inner member 38 can be made from polyimide. These materials and dimensions should be viewed as exemplary only, as those skilled in the art would appreciate the applicability of alternative dimensions and materials for these elements.

An outer sheath 58 may surround outer tube 34 to define an annular lumen 60 between sheath 58 and tube 34. Sheath 58 preferably extends from cooling member 18 proximally to a manifold. The manifold for this embodiment can include an additional port in fluid communication with lumen 60. Except for the additional port, lumen 60 should be completely sealed such that a vacuum may be maintained within lumen 60 when a vacuum source is applied thereto. A vacuum can be created in lumen 60 during the procedure to provide insulation between the coolant and the patient. Sheath 58 can be made from biocompatible materials known to those skilled in the art of catheter construction which are sufficiently rigid to prevent lumen 60 from collapsing when a vacuum is created therein.

Cooling member 18 can be advanced across a lesion in a conventional manner. Coolant may then be released into inner member 38 from a pressurized container or pump (not shown) through intake tube 46 to cool the adjacent lesion at a rate appropriate to the treatment goals described in more detail below. Preferably, coolant may be sprayed onto inner member 38 through intake tube 46, a sprayer, or other suitable elements. The coolant is discharged from inner member 38 through drain lumen 52. Inner member 38 may be inflated (i.e., by coolant) to a relatively low pressure. For example, inner member 38 may be inflated to 0.5–2.0 atmospheres. Cooling may drop the temperature of the tissue at an area of interest to about −20° C. to −81° C. and occur over about 1 to 5 minutes, preferably about 2 minutes.

In a preferred embodiment of the invention, the inflation fluid is a low freezing point liquid such as an ethanol mixture or a liquefied gas such as $N_2O$ or $CO_2$. The coolant is one which will provide the appropriate heat transfer characteristics consistent with the goals of treatment. Liquid $N_2$ can be used as a general purpose coolant with cryo balloon therapy apparatus 10 and is particularly useful when freezing of cells within the lesion is desired. When liquid $N_2$ is used in a cryo balloon therapy apparatus, it can be transported to inner member 38 in the liquid phase where it evaporates at orifice 54 and exits through lumen 52 as a gas. Freon, $N_2O$ gas, and $CO_2$ gas can also be used as coolants. Other coolants could be used such as cold saline solution which would enter and exit inner member 38 as a liquid, Fluisol or a mixture of saline solution and ethanol. It is anticipated that coolants such as saline solution could be used with cryo balloon therapy apparatus 10 when rapid freezing of cells within a lesion is not a treatment goal. One skilled in the art would appreciate that other coolants could be used in a similar manner to achieve one or more of the treatment goals.

According to a preferred embodiment, liquid $N_2O$ may be sprayed from intake tube 46 onto inner member 38. Alternatively, liquid $CO_2$ may be sprayed onto inner member 38. Preferably, regulated back pressure may be maintained along the path followed by the coolant in order to prevent freezing of coolant (i.e., dry ice formation) within catheter 12. Cryo balloon therapy apparatus 10 may then be used to cool (i.e., freezing, causing cold-induced lesions, etc.) an area of interest, for example the pulmonary vein. During treatment, the size and depth of orifices generated at the area of interest may be measured both before and after ablation by a number of imaging techniques including intracardiac ultrasound.

Cooling may be the result of both the Joule-Thompson effect and the latent heat of vaporization. The Joule-Thompson effect is defined as the cooling effect that comes about when a highly compressed non-ideal gas expands into a region of low pressure. The latent heat of vaporization is defined as the heat that is released as the result of the phase change from a liquid to a gas. It is believed that the latent heat of vaporization contributes to the majority of the cooling with cryo balloon therapy apparatus 10.

Inner member 38 may be maneuvered into position in a number of ways. For pulmonary vein ablation, for example, inner member 38 may be guided to the pulmonary vein through a guiding sheath. When inner member 38 is positioned within the pulmonary vein, the guiding sheath may then be withdrawn. The stability and position of inner member 38 may be assessed by contrast injection and low pressure inflation of inner member 38. Moreover, transesophageal echocardiography may be used to monitor for gas leakage, balloon position, and stability. A recording catheter (e.g., a thirty two electrode recording catheter) may be used to assay the electrical activity from the left atrium to the pulmonary vein, the pulmonary vein to left atrium conduction, and the pacing threshold before and after ablation.

When used for pulmonary vein ablation, cryo balloon therapy apparatus 10 may be placed within the pulmonary vein and inflated so as to substantially occlude the pulmonary vein. A contrasting agent may be released from distal end 16 of catheter 12 and monitored with an appropriate imaging technique in order to verify occlusion of the pulmonary vein. Pulmonary vein ablation may then occur.

It is believed that cryo balloon therapy may lead to intra-tissue hemorrhage, which may lead to the formation of smooth fibrous tissue after completion of the healing process. It is also believed that cryo balloon therapy would not result in shrinkage of venous tissue or collagen build up as may be the case for other ablation techniques. Also, the contractile function of the left atria would be unchanged, unlike radio frequency ablation, which may decrease atrial output. However, it is believed that cryo balloon therapy may lead to the thickening of fibrous tissue within arterial walls. This may suggest that cryo balloon therapy may be efficacious in other vascular treatments including varicose vein treatment of incompetent valves, valvular disease, mitral valve regurgitation therapy, gastric reflux disease, gastro esophageal reflux disease, GURD, esophageal disease, cancer treatment including stomach or uterine cancer, etc.

Figure 3:
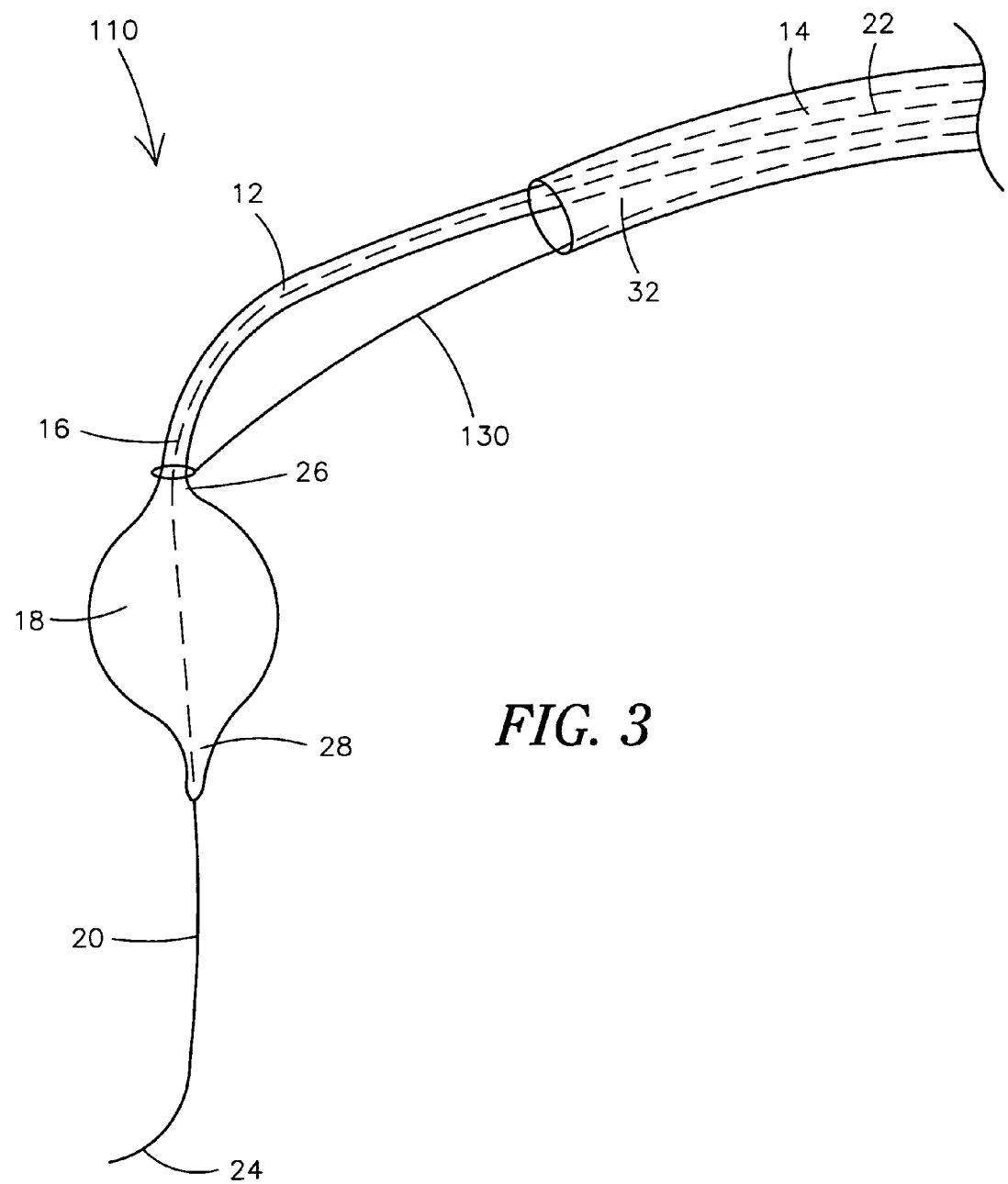
FIG. 3 is a plan view of an alternate cryo balloon therapy apparatus in accordance with the present invention.

FIG. 3 is a plan view of an alternate cryo balloon therapy apparatus according to a preferred embodiment of the current invention. Cryo balloon therapy apparatus 110 is essentially similar to cryo balloon therapy apparatus 10 except that pull cord 130 is coupled to proximal end 26 of cooling member 18.

Figure 4:
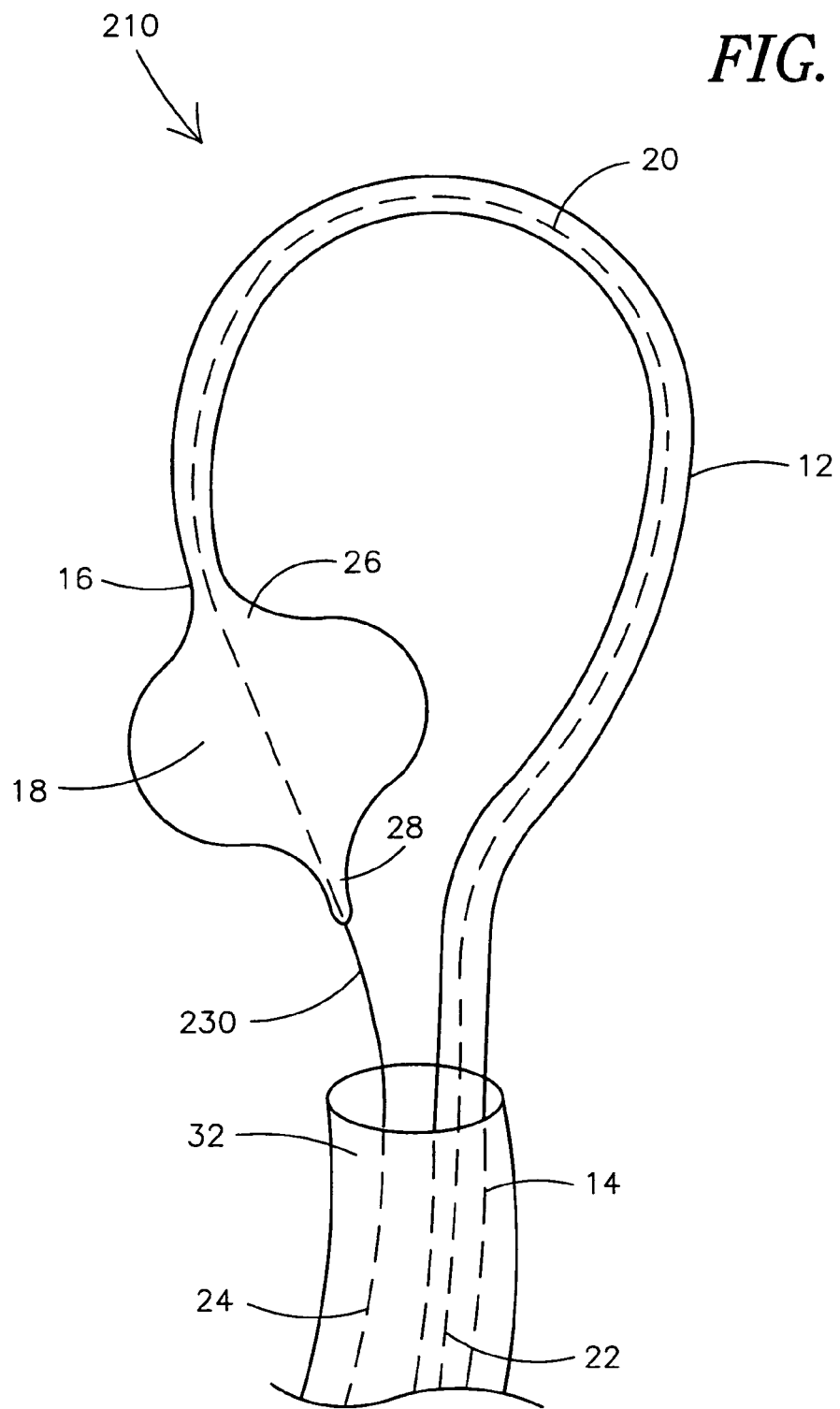
FIG. 4 is a plan view of a second alternate cryo balloon therapy apparatus in accordance with the present invention.

FIG. 4 is a plan view of a second alternate cryo balloon therapy apparatus according to a preferred embodiment of the current invention. Cryo balloon therapy apparatus 210 is essentially similar to cryo balloon therapy apparatus 10 except that pull cord 230 includes guidewire 20. According to this embodiment, guidewire 20 may be manipulated through sheath 32 to control the position of cooling member 18. For example, guidewire 20 may be pulled so as to bend catheter 12 slightly and alter the position of cooling member 18.

Figure 5:
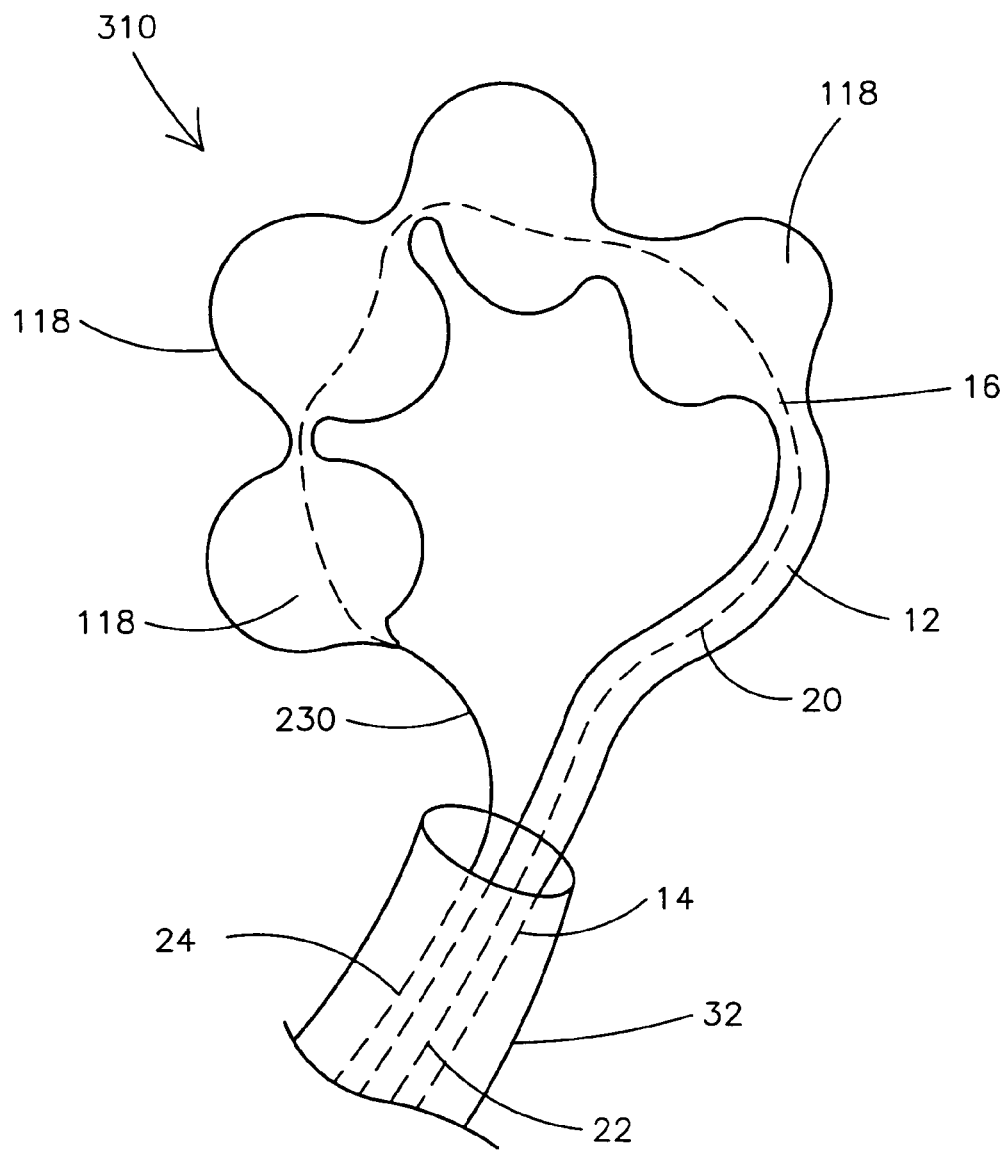
FIG. 5 is a plan view of a third alternate cryo balloon therapy apparatus in accordance with the present invention.

FIG. 5 is a plan view of a third alternate cryo balloon therapy apparatus according to a preferred embodiment of the current invention. Cryo balloon therapy apparatus 310 is essentially similar to cryo balloon therapy apparatus 210 comprising multiple cooling members 118. Multiple cooling members 118 may provide additional heat exchange surfaces that may be beneficial in specific medical procedures.

Figure 6:
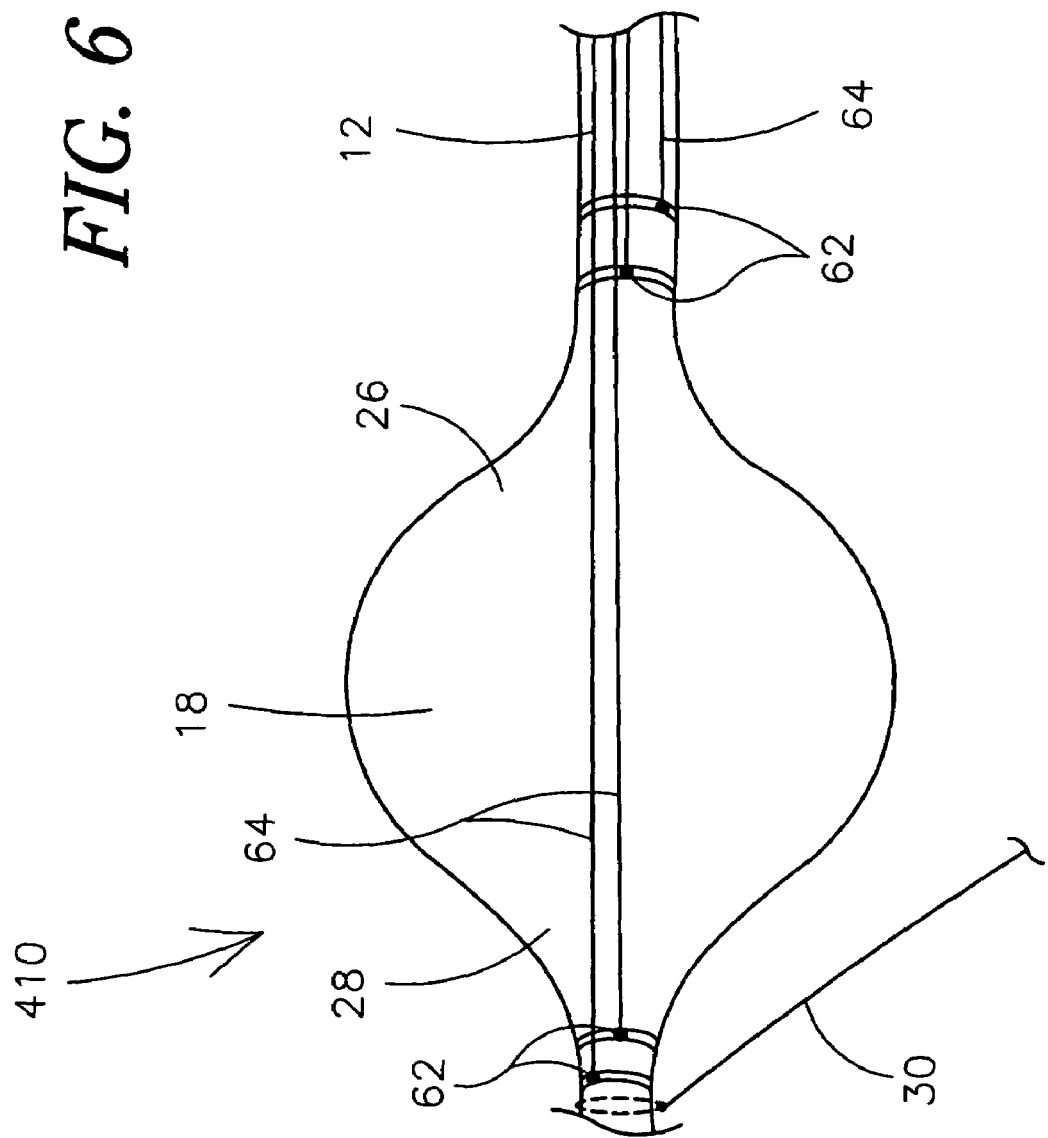
FIG. 6 is a plan view of a fourth alternate cryo balloon therapy apparatus in accordance with the present invention.

FIG. 6 is a plan view of a fourth alternate cryo balloon therapy apparatus according to a preferred embodiment of the current invention. Cryo balloon therapy apparatus 410 is essentially similar to cryo balloon therapy apparatus 10 further comprising at least one electrode 62 having an electrical lead 64. Cooling member 18 may comprise an additional set of at least one electrode 62 having an electrical lead 64. Preferably, electric leads 62 connect to a suitable device.

In a preferred embodiment of the current invention, electrode 62, preferably when used in conjunction with a suitable device, can be used to assess the electrical activity of an area of interest. For example, electrode 62 may be used to determine the electrical state of a region within an atrium. If the atrium is found to have inappropriate electrical activity, a cryo balloon therapy apparatus can be used to treat the atrium.

Figure 7:
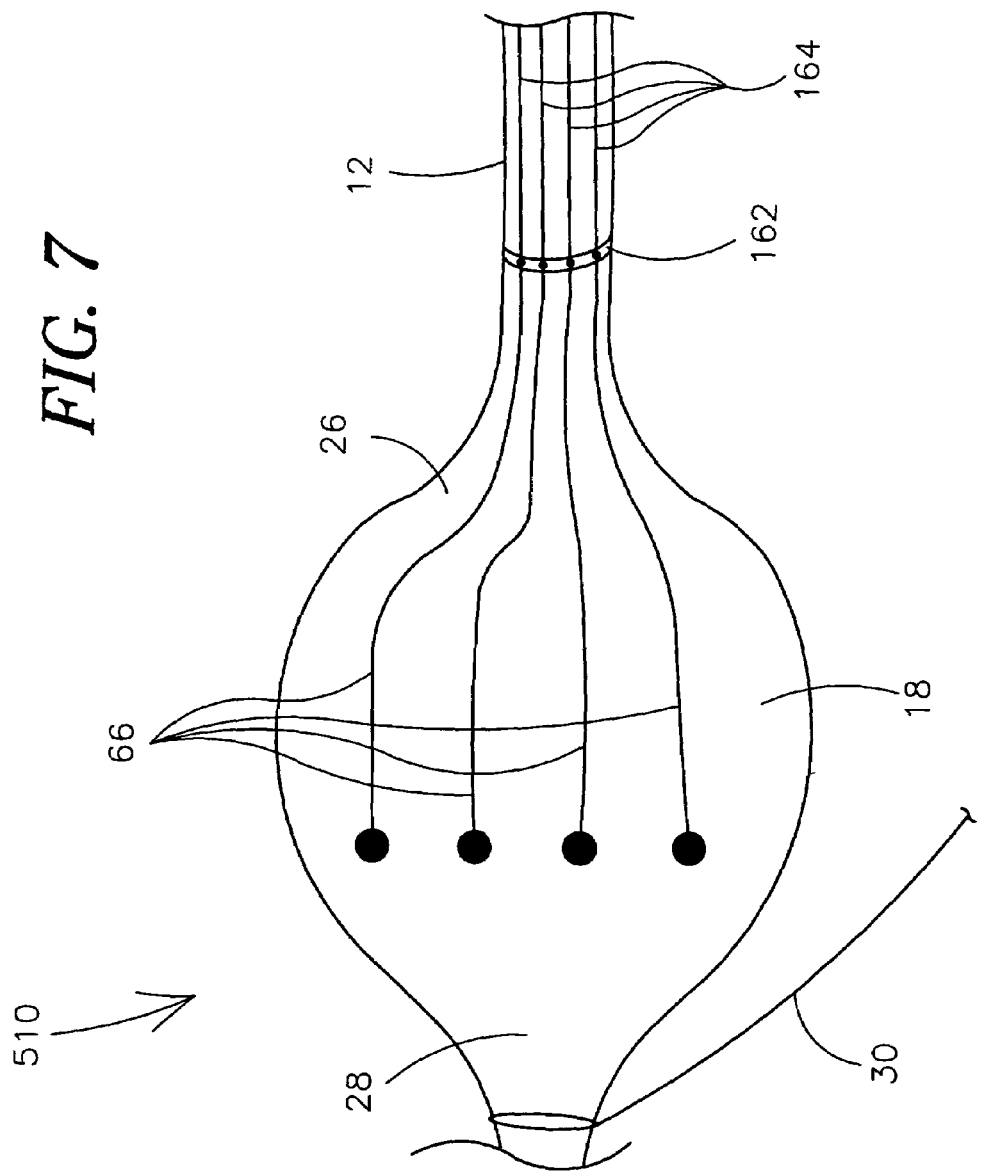
FIG. 7 is a plan view of a fifth alternate cryo balloon therapy apparatus in accordance with the present invention.

FIG. 7 is a plan view of a fifth alternate cryo balloon therapy apparatus according to a preferred embodiment of the current invention. Cryo balloon therapy apparatus 510 is essentially similar to cryo balloon therapy apparatus 10 further comprising a plurality of pad printed conductive electrodes 66. Pad printed electrodes 66 may connect to at least one electrode 162 having an electrical lead 164. Preferably, electric lead 164 connects to a suitable device.

Similar to what is disclosed above, electrode 162, preferably when used in conjunction with a suitable device, can be used to assess the electrical activity of an area of interest. For example, electrode 162 may be used to determine the electrical state of a region within an atrium.

Figure 8:
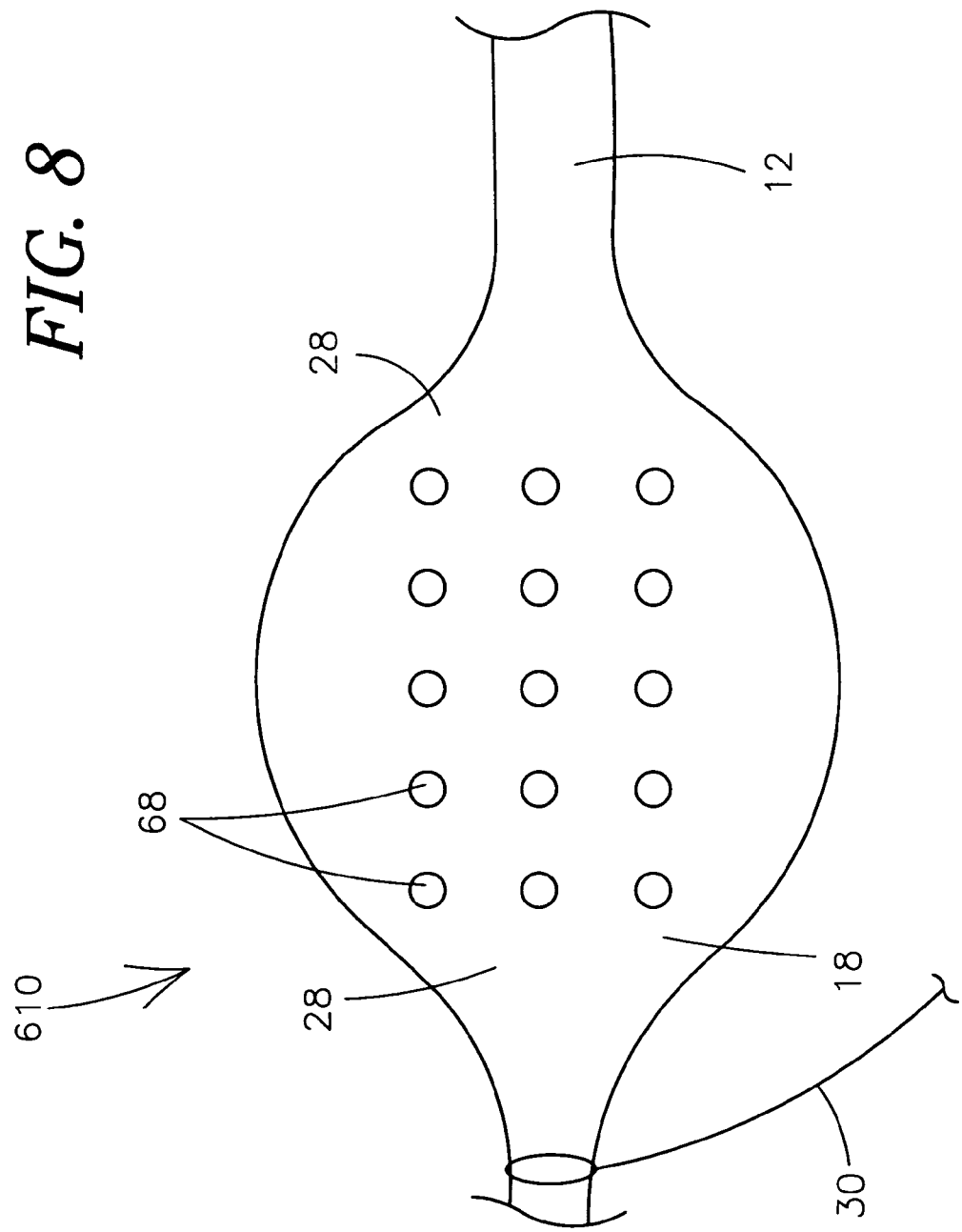
FIG. 8 is a plan view of a sixth alternate cryo balloon therapy apparatus in accordance with the present invention.

FIG. 8 is a plan view of a sixth alternate cryo balloon therapy apparatus according to a preferred embodiment of the current invention. Cryo balloon therapy apparatus 610 is essentially similar to cryo balloon therapy apparatus 10 further comprising a plurality of thermo-resistive sensors 68.

In a preferred embodiment, temperature can be monitored by thermo-resistive sensors 68 either absolutely with pre-calibrated sensors and/or relatively between the sensors. Depending on the treatment goals and temperature level monitored, the flow rate of the coolant into the catheter can be adjusted to raise or lower the temperature of the lesion.

Figure 9:
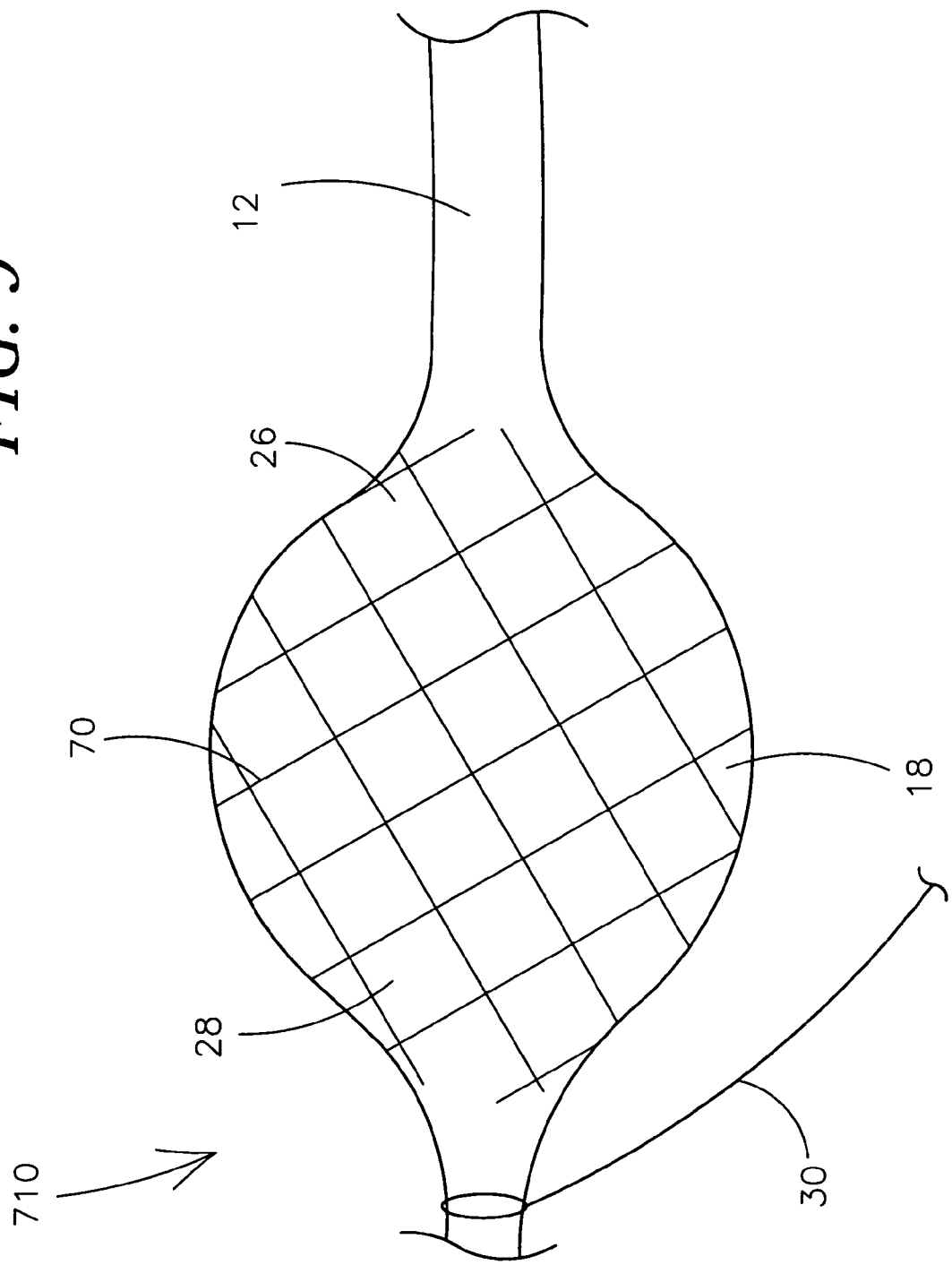
FIG. 9 is a plan view of a seventh alternate cryo balloon therapy apparatus in accordance with the present invention.

FIG. 9 is a plan view of a seventh alternate cryo balloon therapy apparatus according to a preferred embodiment of the current invention. Cryo balloon therapy apparatus 710 is essentially similar to cryo balloon therapy apparatus 10 further comprising a support member 70.

Support member 70 may comprise a plurality of materials including, but not limited to, Kevlar, Spectra, stainless steel, nickel alloy, nickel-titanium alloy, nitinol, etc. Preferably, support member 70 helps to prevent cooling member 18 from rupturing. For example, a Kevlar support member may help make a cryo balloon therapy balloon rupture resistant and able to withstand high pressures. In an exemplary embodiment, support member 70 comprises a sealed jacket that is formed over cooling member 18. Preferably, by forming a seal, support member 70 may add additional safety to cooling member 18 by including a layer capable of preventing leakage of substances from cooling member 18.

Figure 10:
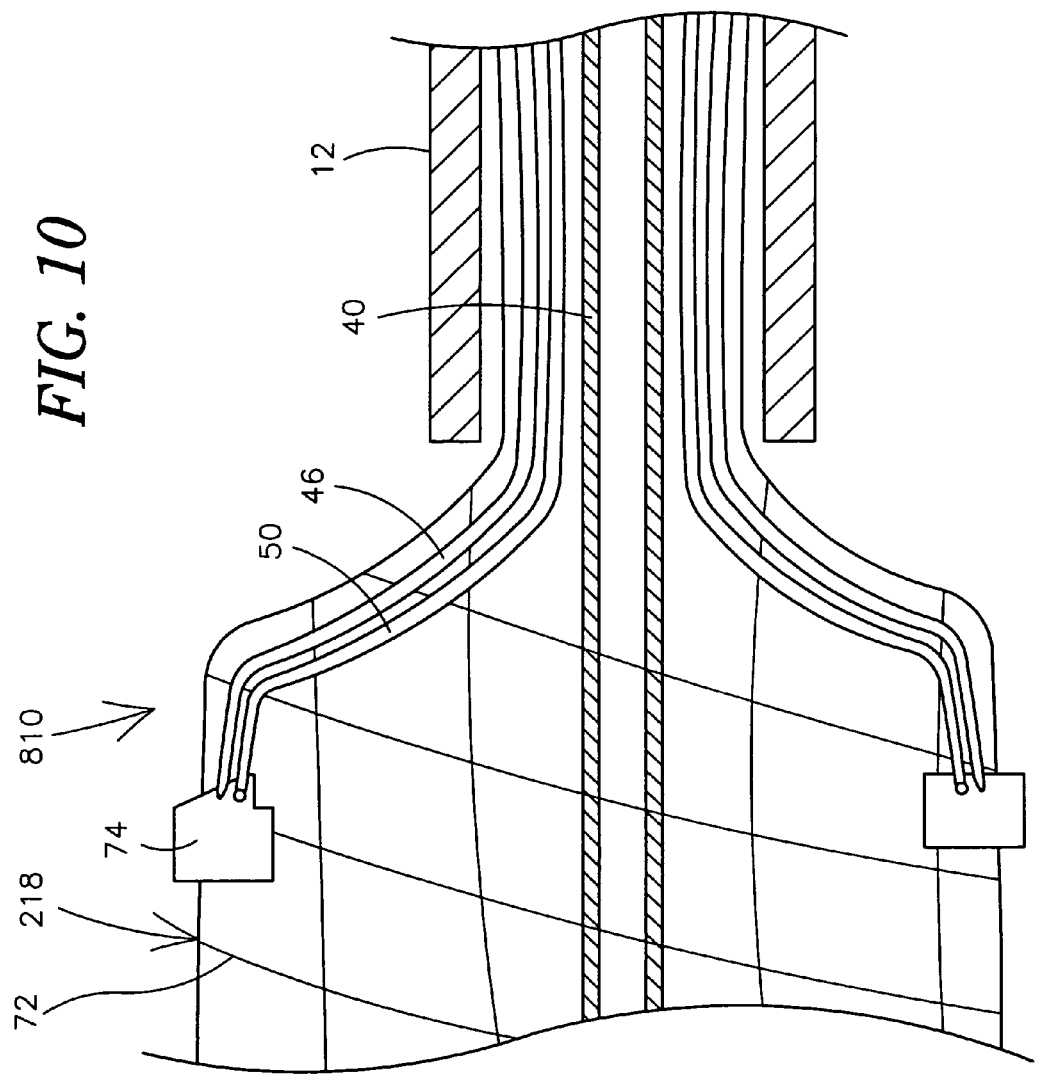
FIG. 10 is a plan view of an eighth alternate cryo balloon therapy apparatus in accordance with the present invention.

FIG. 10 is an eighth alternate embodiment of a cooling member in accordance with the current invention. Cryo balloon therapy apparatus 810 includes an alternate cooling member 218 including a mesh cage 72. Preferably, mesh cage 72 is a self-expanding nitinol braid. Mesh cage 72 may be expanded by retraction of catheter 12 relative to mesh cage 72. In a preferred embodiment, cooling member 218 further comprises at least one cryo balloon therapy chamber 74 coupled to mesh cage 72 and connected to a coolant source by way of a plurality of coolant conduits similar to those shown in FIG. 2.

Cryo balloon therapy chamber 74 may be connected to a coolant source by intake tube 46 and drain tube 50. In use, cryo balloon therapy chamber 74 is cooled by passing coolant through intake tube 46 into cryo balloon therapy chamber 74. Following an appropriate medical procedure, coolant may be drained through drain tube 50.

Figure 11:
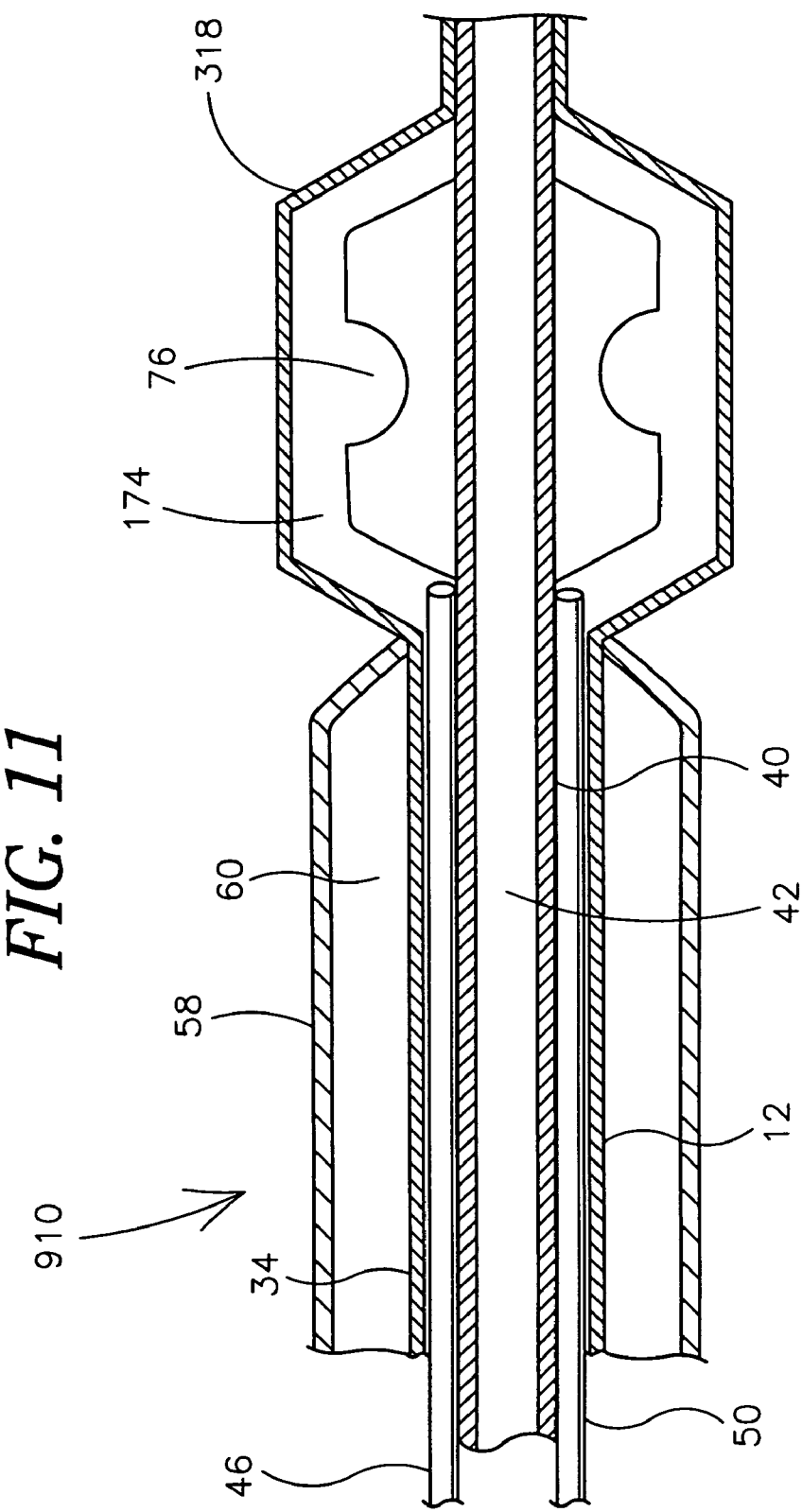
FIG. 11 is a plan view of a ninth alternate cryo balloon therapy apparatus in accordance with the present invention.

FIG. 11 is a ninth alternate embodiment of a cooling member in accordance with the current invention. Cryo balloon therapy apparatus 910 includes an alternate cooling member 318 including cryo balloon therapy chamber 174. In a preferred embodiment, cryo balloon therapy chamber 174 further comprises a cryo balloon therapy ring 76. According to this embodiment, cryo balloon therapy chamber 174 is connected to a coolant source similarly as in devices described above. Coolant may be distributed throughout cryo balloon therapy chamber 174 and concentrate proximate cryo balloon therapy ring 76. Cryo balloon therapy ring 76 may, thus, comprise a preferred surface of cryo balloon therapy apparatus 910 for heat exchange with a target region.

Figure 12:
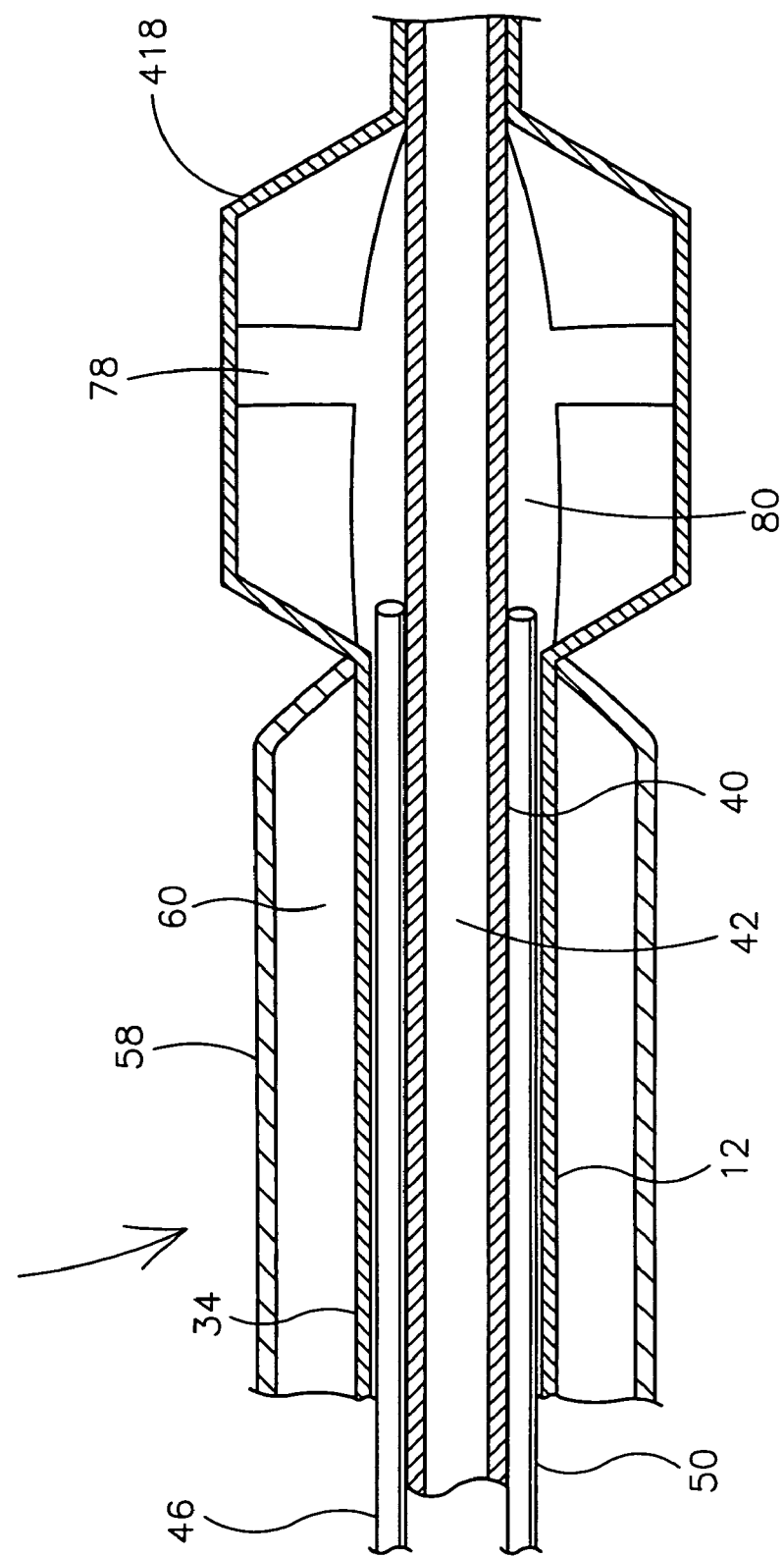
FIG. 12 is a plan view of a tenth alternate cryo balloon therapy apparatus in accordance with the present invention.

FIG. 12 is a tenth alternate embodiment of a cooling member in accordance with the current invention. Cryo balloon therapy apparatus 1010 includes an alternate cooling member 418 including a heat exchange surface 78. In a preferred embodiment, heat exchange surface 78 is connected to a cooling source by a cooling tube 80. Coolant may be distributed to cooling member 418 through cooling tube 80 in a manner similar to devices described above. According to this embodiment, coolant may be distributed throughout cooling tube 80 and concentrate proximate heat exchange surface 78. Heat exchange surface 78 may, thus, comprise a preferred surface of cryo balloon therapy apparatus 1010 for heat exchange with a target region.

Figure 13:
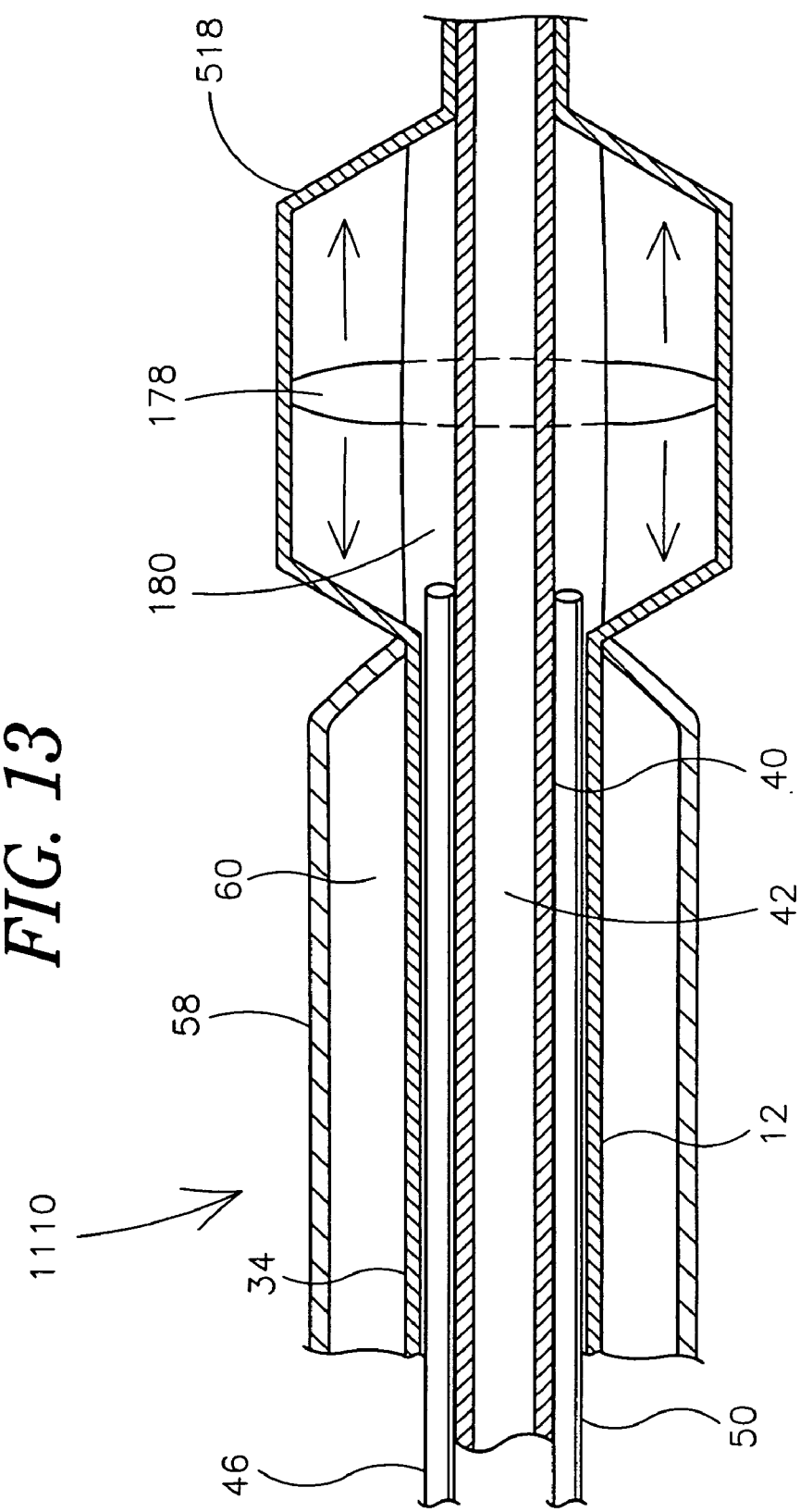
FIG. 13 is a plan view of an eleventh alternate cryo balloon therapy apparatus in accordance with the present invention.

FIG. 13 is an eleventh alternate embodiment of a cooling member in accordance with the current invention. Cryo balloon therapy apparatus 1110 is essentially similar to cryo balloon therapy apparatus 1010 having an alternate cooling member 518 including a slidable heat exchange surface 178. Slidable heat exchange surface 178 may be coupled to cooling tube 180 and slidable along cooling tube 180. According to this embodiment, the location of a heat exchange surface for cooling member 518 may be slidable relative to cooling tube 18. Cooling tube 180 may be connected to a coolant source similarly to devices described above.

Figure 14:
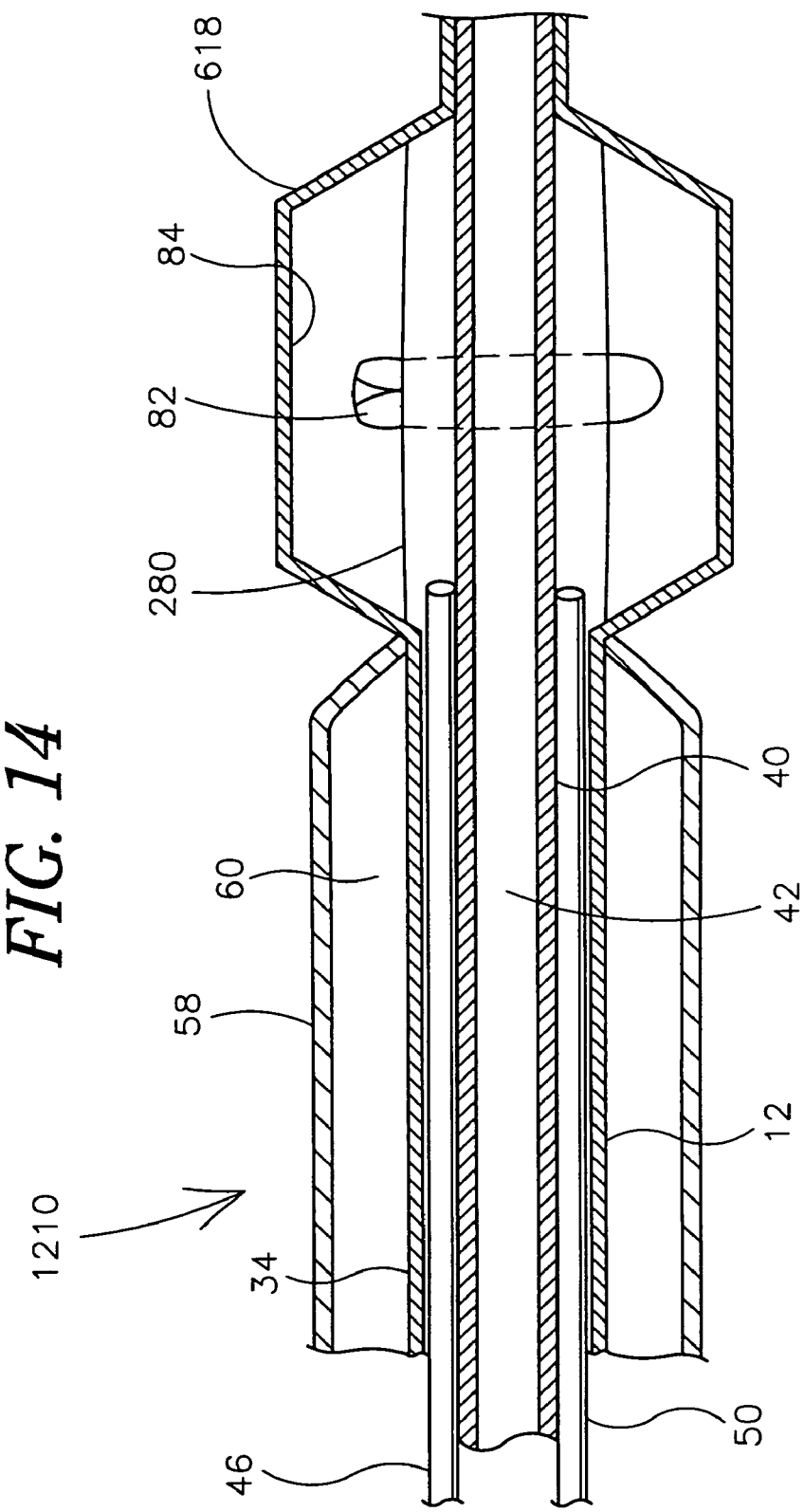
FIG. 14 is a plan view of a twelfth alternate cryo balloon therapy apparatus in accordance with the present invention.

FIG. 14 is a twelfth alternate embodiment of a cooling member in accordance with the current invention. Cryo balloon therapy apparatus 1210 is essentially similar to cryo balloon therapy apparatus 1010 having an alternate cooling member 618 including a slidable and rotatable sprayer 82. Slidable and rotatable sprayer 82 may be coupled to a cooling tube 280 similar to what is disclosed above. Moreover, slidable and rotatable sprayer 82 may be slidable and rotatable relative to cooling tube 280. Cooling tube 280 may be connected to a coolant source similarly to devices described above.

Cooling tube 280 includes means to transfer coolant from a coolant source to slidable and rotatable sprayer 82 so that coolant may be sprayed from slidable and rotatable sprayer 82 onto an inner surface 84 of cooling member 618. In an exemplary embodiment, slidable and rotatable sprayer 82 is slidable along cooling tube 280.

According to a preferred embodiment, liquid $N_2O$ may be sprayed from slidable and rotatable sprayer 82 onto inner surface 84 of cooling member 618 in a manner similar to what is described above. Spraying coolant directly onto inner surface 84 may be the preferred method of delivering coolant to cooling member 618. Moreover, sprayer 82 may be incorporated into alternative embodiments of cryo therapy apparatuses described above without departing from the spirit of the invention.

FIG. 15 is a thirteenth alternate embodiment of a cooling member in accordance with the current invention. Cryo balloon therapy apparatus 1310 includes an alternate cooling member 718 including a cryo balloon therapy assembly 86. Cryo balloon therapy assembly 86 may be connected to cooling tube 380 similarly to what is described above.

Cryo balloon therapy assembly 86 further comprises a mesh 88 and an outer surface 90. Preferably, outer surface 90 comprises a sponge-like material. In use, coolant may be transferred to mesh 88 through cooling tube 380 similarly to what is disclosed above. Outer surface 90 may aid heat transfer. For example, if the coolant comprises a liquid, outer surface 90 may aid heat transfer by staying wet after coolant is used, evaporates, or is drained.

In use, cryo balloon therapy may include the use of any of the cryo balloon therapy apparatuses described to treat a number of medical conditions as described above. For example, cryo balloon therapy may be used to treat atrial fibrillation. Cryo balloon therapy of the pulmonary vein may not be associated with pulmonary vein stenosis, which may be the case in other ablative techniques (e.g., radiofrequency ablation). Moreover, cryo balloon therapy may potentially be safer than radiofrequency ablation.

Numerous advantages of the invention covered by this document have been set forth in the foregoing description. It will be understood, however, that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A cryoplasty apparatus, comprising:
   a catheter having a proximal and a distal end;
   a cooling member disposed at the distal end of the catheter;
   a pull cord arranged to pull the cooling member proximally; and
   a sheath that couples the pull cord and the catheter.

2. The cryoplasty apparatus in accordance with claim 1, wherein the cooling member includes a balloon.

3. The cryoplasty apparatus in accordance with claim 1, wherein the cooling member further comprises at least one electrode.

4. The cryoplasty apparatus in accordance with claim 1, wherein the cooling member further comprises at least one pad printed conductive electrode.

5. The cryoplasty apparatus in accordance with claim 1, wherein the cooling member further comprises at least one thermo-resistive sensor.

6. The cryoplasty apparatus in accordance with claim 1, wherein the cooling member further comprises a support member.

7. The cryoplasty apparatus in accordance with claim 1, wherein the cooling member further comprises a mesh cage and at least one cryoplasty chamber.

8. The cryoplasty apparatus in accordance with claim 1, wherein the cooling member further comprises a cryoplasty ring.

9. The cryoplasty apparatus in accordance with claim 1, wherein the cooling member further comprises a heat exchange surface connected to a cooling tube.

10. The cryoplasty apparatus in accordance with claim 9, wherein the heat exchange surface is slidable.

11. The cryoplasty apparatus in accordance with claim 1, wherein the cooling member further comprises a slideable and rotatable sprayer.

12. The cryoplasty apparatus in accordance with claim 1, wherein the cooling member further comprises a cryoplasty assembly, the cryoplasty assembly comprising a mesh and an outer surface.

13. The cryoplasty apparatus in accordance with claim 1, wherein the pull cord extends from a distal end of the cooling member.

14. The cryoplasty apparatus in accordance with claim 1, wherein the pull cord is disposed on the cooling member.

15. The cryoplasty apparatus in accordance with claim 1, wherein the catheter is at least in part surrounded by an insulating sheath which in part defines a vacuum lumen.

16. A cryoplasty apparatus, comprising:
    a catheter having a proximal end and a distal end, the catheter defining an inflation lumen, a coolant intake lumen, and exhaust lumen therethrough, each lumen having a proximal end and a distal end proximate the proximal and distal ends of the catheter respectively;
    a cooling member disposed at the distal end of the catheter and in fluid communication with the inflation lumen;
    a pull cord arranged to pull the cooling member proximally; and
    a sheath that couples the pull cord and the catheter and includes a first lumen for the pull cord and a second lumen for the catheter.

17. The cryoplasty apparatus in accordance with claim 16, further comprising a source of coolant being connected to the proximal end of the catheter in fluid communication with the intake lumen.

18. The cryoplasty apparatus in accordance with claim 17, wherein the coolant source is liquid $N_2$.

19. The cryoplasty apparatus in accordance with claim 16, wherein the catheter further defines a guidewire lumen.

20. The cryoplasty apparatus in accordance with claim 16, wherein the cooling member further comprises at least one electrode.

* * * * *